US010098543B2

(12) United States Patent
Kinkingnehun et al.

(10) Patent No.: US 10,098,543 B2
(45) Date of Patent: Oct. 16, 2018

(54) METHOD AND SYSTEM FOR REVEALING OCULOMOTOR ABNORMALITIES

(75) Inventors: Serge Kinkingnehun, Vitry sur Seine (FR); Mickael Maillard, Puteaux (FR); Mathieu Argudo, Hendaye (FR); Sophie Rivaud-Pechoux, Saint-Germain-sur-Ecole (FR)

(73) Assignee: SURICOG, SAS, Paris (FR)

( * ) Notice: Subject to any disclaimer, the term of this patent is extended or adjusted under 35 U.S.C. 154(b) by 837 days.

(21) Appl. No.: 13/258,033

(22) PCT Filed: Mar. 31, 2010

(86) PCT No.: PCT/FR2010/050610
§ 371 (c)(1),
(2), (4) Date: Sep. 21, 2011

(87) PCT Pub. No.: WO2010/112771
PCT Pub. Date: Oct. 7, 2010

(65) Prior Publication Data
US 2012/0022395 A1 Jan. 26, 2012

(30) Foreign Application Priority Data
Apr. 1, 2009 (FR) ..................................... 09 52102

(51) Int. Cl.
*A61B 3/14* (2006.01)
*A61B 3/113* (2006.01)

(52) U.S. Cl.
CPC .............. *A61B 3/145* (2013.01); *A61B 3/113* (2013.01)

(58) Field of Classification Search
CPC ................................ A61B 3/145; A61B 3/113

USPC ................................ 600/544, 558, 559, 595
See application file for complete search history.

(56) References Cited

U.S. PATENT DOCUMENTS

| | | | |
|---|---|---|---|
| 4,889,422 A | 12/1989 | Pavlidis | |
| 5,874,471 A | 2/1999 | Waugh | |
| 6,231,187 B1 | 5/2001 | Munoz | |
| 7,460,940 B2 * | 12/2008 | Larsson et al. | 701/49 |

(Continued)

FOREIGN PATENT DOCUMENTS

| | | |
|---|---|---|
| FR | 2593381 | 7/1987 |
| JP | 2003319907 | 11/2003 |
| WO | 2005094667 | 10/2005 |

OTHER PUBLICATIONS

Van Stockum et al., "Don't look now or look away: Two sources of saccadic disinhibition in Parkinson's disease?" Neuropsychologia, Pergamon Press, Oxford GB, vol. 46, No. 13, Nov. 1, 2008, pp. 3108-3115.

(Continued)

*Primary Examiner* — Sean Dougherty
(74) *Attorney, Agent, or Firm* — Young & Thompson

(57) ABSTRACT

System for demonstrating oculomotor abnormalities in a eukaryote, the system including: —elements for capturing (13) the eye movements made by the eukaryote while the eukaryote is stimulated with at least one image in accordance with at least one instruction, wherein the capture elements (13, 14) supply a capture signal, —an analysis module (18) for calculating the value of at least one predetermined parameter by analysis of the capture signal, and —elements (22) for determining an abnormality as a function of the calculated value at least one predetermined value for each of the parameters.

19 Claims, 2 Drawing Sheets

(56) References Cited

U.S. PATENT DOCUMENTS

| | | | | |
|---|---|---|---|---|
| 7,682,024 | B2* | 3/2010 | Plant et al. | 351/209 |
| 7,892,180 | B2* | 2/2011 | Epley | 600/559 |
| 2004/0097839 | A1* | 5/2004 | Epley | 600/595 |
| 2004/0181168 | A1* | 9/2004 | Plant et al. | 600/558 |
| 2005/0073136 | A1* | 4/2005 | Larsson et al. | 280/735 |
| 2005/0124983 | A1* | 6/2005 | Frey et al. | 606/5 |
| 2006/0028400 | A1* | 2/2006 | Lapstun et al. | 345/8 |
| 2006/0087618 | A1* | 4/2006 | Smart | A61B 3/005 351/222 |
| 2008/0009772 | A1* | 1/2008 | Tyler et al. | 600/595 |
| 2009/0021695 | A1* | 1/2009 | Scarpino | 351/210 |
| 2009/0036755 | A1* | 2/2009 | Pradeep et al. | 600/301 |
| 2009/0156955 | A1* | 6/2009 | Jung et al. | 600/544 |
| 2010/0033333 | A1* | 2/2010 | Victor et al. | 340/576 |
| 2010/0268125 | A9* | 10/2010 | Epley | 600/595 |
| 2011/0170065 | A1* | 7/2011 | Sugio et al. | 351/209 |
| 2014/0184550 | A1* | 7/2014 | Hennessey et al. | 345/173 |

OTHER PUBLICATIONS

International Search Report dated Jun. 28, 2010, in corresponding PCT application.

Dejong et al: "Renal arginine metabolism in fasted rats with short bowel syndrome", Clinical Sciences, 1998, vol. 95, pp. 409-418.

* cited by examiner

METHOD AND SYSTEM FOR REVEALING OCULOMOTOR ABNORMALITIES

The invention relates to a system for revealing oculomotor abnormalities in a eukaryote, animal subjects or human subjects.

The field of the invention is the field of the detection and revealing of oculomotor abnormalities in a eukaryote and more particularly the oculomotor abnormalities linked to neurological, psychiatric and neurodevelopmental diseases, as well as the effectiveness and the follow-up of care.

In the case of neurodegenerative diseases, the aging of the population in France is causing a significant increase in the number of patients suffering from these pathologies. Parkinson's disease is the second most prevalent neurodegenerative disease in France with more than 100 000 cases and 10 000 new cases per year.

The term "Parkinson's syndrome" includes Parkinson's disease and the neurological pathologies whose symptoms, at an early stage of the disease, are similar to Parkinson's disease.

Studies conducted on more than 6000 patients suffering from neurological diseases have enable a link to be established between Parkinson's syndromes and certain oculomotor abnormalities, which are measurable thanks to appropriate tests.

At present it is difficult to differentiate the Parkinson's syndromes from each other. A panel of neurologists, in a specialist neurological examination center, is able to distinguish between some of these pathologies, using batteries of in-depth tests and generally having recourse to several complementary investigations, including MRI and scintigraphy. This requires hospitalization of the patient for several days, with a diagnosis time of several months, since the wait for an MRI examination may take up to 6 months and a new appointment with a specialist several more months.

Lastly, an MRI service or a laboratory are expensive and require several operators, which makes this type of diagnosis inaccessible for a neurologist operating privately.

Currently, no apparatus exists making it possible to reveal oculomotor abnormalities linked to Parkinson's syndromes and more generally to neurological, psychiatric or neurodevelopmental diseases in a eukaryote, as well as to evaluate the effect of care and the follow-up thereof. The system of the invention constitutes a technological platform comparable to a companion test.

An object of the present invention is to mitigate the drawbacks indicated above.

Another object of the present invention is to provide an automated method and a system for detecting or revealing oculomotor abnormalities that are more effective than the systems and methods of the prior art.

It is a further object of the invention to provide a system enabling a neurologist, a psychiatrist or a specialist to be assisted in revealing oculomotor abnormalities.

Still another object of the invention is to provide a system for revealing oculomotor abnormalities enabling faster revealing of abnormalities.

Lastly, an object of the invention is to provide a system making it possible to reveal oculomotor abnormalities more cheaply than current practices.

The invention enables the aforementioned objects to be attained by a system for revealing oculomotor abnormalities in a human or animal eukaryote, said system comprising:

means for capturing movements of the eye of said eukaryote in the "native" state or while said eukaryote is stimulated by at least one image in accordance with at least one instruction.

an analysis module for computing the value of at least one predetermined parameter by analysis of said captured movements, and means for determining an abnormality on the basis of said computed value and at least one predetermined value for each of the parameters.

It is possible for said system the case arising to be associated with means for generating at least one stimulation of at least one visual cell of said eukaryote subject and the case arising also to comprise means for displaying said stimulation images.

In the present application, "eukaryote" designates a human subject or an animal subject.

The system according to the invention enables oculomotor abnormalities to be determined in a fully automated manner by analyzing the ocular movements that are induced, in accordance with at least one instruction, by at least one stimulation image. On the basis of the ocular movements one or more parameters are computed and compared to predetermined values. This comparison enables it to be determined whether the eukaryote presents ocular abnormalities and if so with which pathology its abnormalities may be associated.

As the system according to the invention is fully automated, it does not require the involvement of a specialist and still less so the involvement of a panel of specialists as is currently the case. This makes it possible to reduce the time and the costs for revealing abnormalities.

Furthermore, the revealing of ocular abnormalities may be carried outside specialist premises, for example at those of the healthy eukaryote. Thus, the system according to the invention makes it possible to avoid mobilizing an MRI or a laboratory and the associated staff which enables further reduction in the costs of revealing abnormalities.

Lastly, the system according to the invention enables the abnormalities in ocular movements to be determined more rapidly than in current practice. The tests carried out show that the revealing of ocular abnormalities in a eukaryote may be performed on average in 15 minutes instead of several hours currently. Revealing abnormalities more rapidly is very important for the health of the eukaryote since it enables faster operation on the eukaryote.

Furthermore, the system according to the invention reveals abnormalities with a non-invasive visual examination and which is thus less of a constraint for the eukaryote than the current invasive operations.

The visual stimulation may comprise a set of stimulation images or a set of visual animations. Thus the system according to the invention may comprise:

means for generating at least one visual stimulation of at least one visual cell of said eukaryote, and means for displaying said stimulation images.

Advantageously, the analysis module may comprise a sub-module that reveals saccades.

Furthermore, the analysis module may further comprise a sub-module for revealing and eliminating artefacts to facilitate the automatic reading and analysis of the oculomotor trace.

An example of the revealing of saccades, and an example of revealing and eliminating artefacts, are described later.

The system according to the invention may advantageously further comprise means provided for determining a probability of pathology in said eukaryote on the basis of the computed value and at least one predetermined value for at least one parameter. To be precise, depending on the value computed for one or more parameters and one or more predetermined threshold values for that parameter or those parameters, a probability of pathology may be determined for the eukaryote, for example concerning Parkinson's disease.

According to the invention, the means for capturing the movements of the eukaryote's eye may advantageously comprise at least one sensor arranged to capture the oculomotor movements of said eye while said eukaryote is stimulated by said images in accordance with at least one instruction. Such a sensor may for example be a camera and more particularly an infrared camera.

The system according to the invention may furthermore comprise a transformation module performing the transformation of the eye movements into positions on the visual stimulation display means.

The transformation of the eye movements into positions may, in a first embodiment, be carried out in real time, that is to say within a lapse of time less than the display time of the stimulation images, for example less than 16 ms which is the current standard. Thus, when the eukaryote's eye moves over the display means, the position of the eye is computed in real time on the basis of data supplied by the sensor arranged to capture the oculomotor movements.

In a second embodiment, the transformation may be carried out subsequently. In this case the images captured by the camera, for example an infrared camera, are, in a first phase, stored in memory means. In a second phase, for example at the end of the stimulation of the eukaryote's visual cell, the captured images are transformed by the transformation module into positions on the display means.

The analysis module may advantageously be arranged to determine the value of at least one of the parameters chosen from the following list:
  latencies and velocities of horizontal saccades (reaction time of the eukaryote to the appearance of a stimulus),
  precision of the saccades (distance to the target),
  number of intermediate saccades,
  number of errors,
  presence of square waves (isolated saccades which interrupt fixation very briefly with fast return to that fixation),
  presence of nystagmus (an involuntary saccaded oscillatory movement of the eyeball),
  pursuit gain: during ocular pursuit, the slip of the image of the visual target on the retina induces an ocular movement of the same amplitude to maintain that projection on the macula.
  pursuit phase shift,
  quality of pursuit,
  This list is of course not exhaustive.

A saccade is defined as follows: when a new image is selected, the fast ocular movements or saccades enable the point of fixation to be changed.

The values of these parameters, as well as the values of other parameters, may be determined for example by studying the positions of the eukaryote's eye and of the stimulation image or images or that or those targeted on the basis of the stimulation images and instructions associated with those stimulation images. In a particular example that is in no way limiting, the instruction received by the eukaryote may be to look at an opposite position to a point displayed by the display means.

The display means may possibly comprise a touch screen on which a eukaryote is caused to point to a position or to participate in any other interaction on the basis of instructions given in advance.

The system according to the invention may furthermore comprise memory means for storing ocular movements and/or values of the parameters that have been computed and which are linked to the analysis module and/or to the transformation module.

The system according to the invention may furthermore comprise means for displaying results of the tests, as well as means for writing the results to a medium.

In a particular embodiment, the system according to the invention may advantageously take the form of a portable one-piece assembly. The system according to the invention may for example take the form of binoculars, glasses or a glasses frame, so that it can be worn easily by the eukaryote itself.

In another embodiment, the system according to the invention may for example take the form of a carriage movable on rolling means. For example in the context of use in a medical situation.

The system according to the invention may furthermore comprise memory means for storing and preserving the data obtained and possibly means for comparative analysis of the data collected.

The system according to the invention may furthermore comprise display means enabling an operator or specialist to visually display the results relative to several tests carried out over time for the same subject or the results relative to several tests carried out on different subjects for the purpose of making a comparison between those results.

The system according to the invention may take the form of a technology platform comprising display means.

According to another aspect of the invention, a method of revealing oculomotor abnormalities in a eukaryote is provided, said revealing method comprising the following steps:
  capturing movements of the eye of said eukaryote with capturing means while said eukaryote is stimulated by at least one image in accordance with at least one instruction, said capturing means supplying a capture signal,
  analyzing said capture signal to compute the value of at least one predetermined parameter, and
  determining an abnormality on the basis of said computed value and at least one predetermined value for each of the parameters.

The method according to the invention may further comprise the following steps:
  generating at least one image for stimulation of at least one visual cell of said eukaryote, and
  displaying said stimulation image on display means.

The method according to the invention may advantageously comprise a step of transforming movements of the eye into positions on the means for displaying the stimulation images. This transformation step may be carried out in real time at the same time as the capture.

Furthermore, the analysis step may advantageously comprise revealing at least one saccade in the capture signal.

The capturing step may also comprise revealing at least one artefact in the capture signal and eliminating said detected artefact so as to improve the analysis of the signal and thus the revealing of oculomotor abnormalities.

Other advantages and characteristics of the invention will appear on studying the detailed description of an embodiment which is in no way limiting, and of the accompanying drawings, in which:

FIG. 1 is a diagram of an example embodiment of a system according to the invention.

Figure 1:
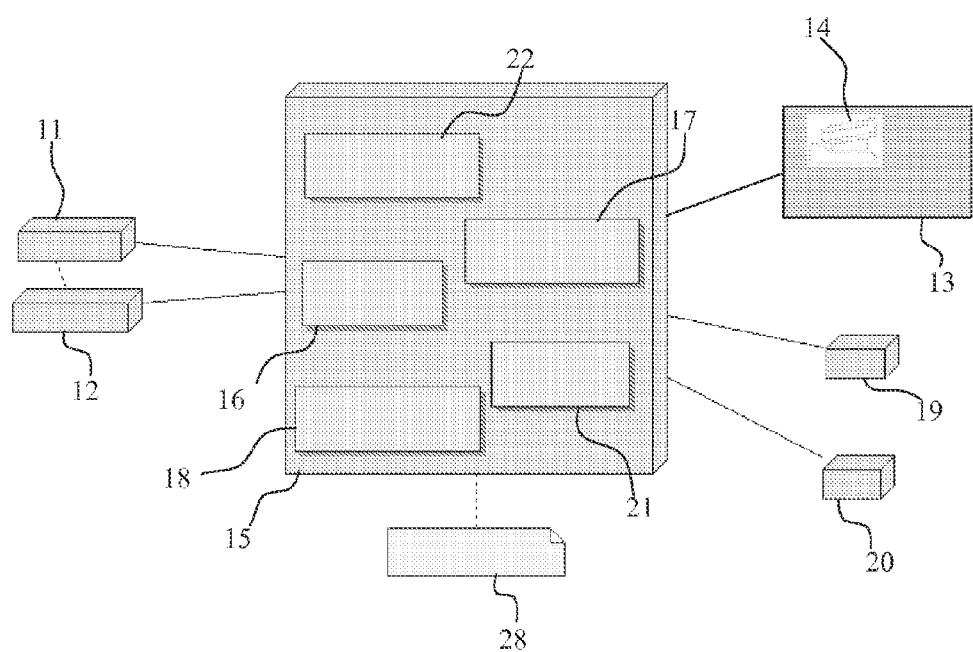
FIG. 1 is a diagram of an example embodiment of the system according to the invention.

The system shown in FIG. 1 comprises a screen 11 for the display of stimulation images (stimuli or tests). This screen may be an LCD flat screen displaying a resolution of 1920×1200 pixels for a 16/9 format of 22" size with a display latency of 2 ms at most.

The system may furthermore comprise a screen 12 enabling the tests to be monitored by a practitioner. This screen 12 may be an LCD flat screen capable of displaying a resolution for example of 1920×1200 pixels.

The system further comprises a device 13 for capturing oculomotor movements. This device may comprise a means for capturing, recording and preserving data (not shown). Such a device 13 may be a monocular or binocular device.

The movement capturing device 13 described here comprises a camera 14 which captures and records the oculomotor movements.

The screens 11 and 12 and the device 13 for capturing oculomotor movements of the eukaryote are linked to a central processing unit 15 either by wire or wirelessly. The central processing unit comprises a module 16 for generating stimuli, a module 17 for transforming ocular movements into positions on the stimuli display screen 11 and a module 18 for analyzing the ocular movements.

The central processing unit 15 may have the following features:
a processor,
RAM memory: greater than or equal to 2 Gb,
Acquisition card for the interface with the device 13, and
Graphics card: standard model whose performance is at least equal to that of an NVidia quadro fx 4100.

The system may further comprise means such as a keyboard 19 for entering data and a mouse 20 for selecting a stimuli test from a among a plurality of tests.

The system according to the invention further comprises memory means 21 for storing stimuli tests capable of being selected for example using the mouse 20, where appropriate means for comparative analysis with other signals for example signals from a healthy eukaryote.

Moreover, the system represented in FIG. 1 further comprises a diagnosis assistance module 22 making it possible to determine a probability for a pathology and to provide a list of pathologies classified according to their probability on the basis of the test results supplied by the analysis module 18.

The system may be connected to another apparatus 23 directly or via a communication network, such as the Internet for example. The apparatus 23 may be a database or any other medical apparatus.

The ocular tests are controlled from the central processing unit 15. They are generated by the generating module 16 and are displayed on the screen 11. The eukaryote looks at those tests with instructions while the camera 14 records the oculomotor movements of the eukaryote. The oculomotor movements are instantaneously transformed into eye positions on the screen 11 by the module 17. The module 17 transforms the capture signal supplied by the capturing device 13 and supplies in turn a "position signal" indicating the positions of the eye on the screen 11 at any time. This capture signal is recorded by the central processing unit in the storage means 21. At the end of the tests, the recordings are automatically analyzed by the analysis module 18 and may then be interpreted by the interpreting and diagnosis assistance module 22.

Module 16 for generating the stimuli comprises a plurality of visual stimuli tests. This module 16 is furthermore adapted for the design and memory storage of new tests by a practitioner.

The analysis of the ocular movements is carried out automatically and supervised by the analysis module 18.

The parameters thus measured may then be interpreted by the diagnosis assistance module 22 which may comprise artificial intelligence which will propose a probability index for the purpose of classifying the eukaryote's disease or diseases or interpreted directly by a specialist.

Figure 2:
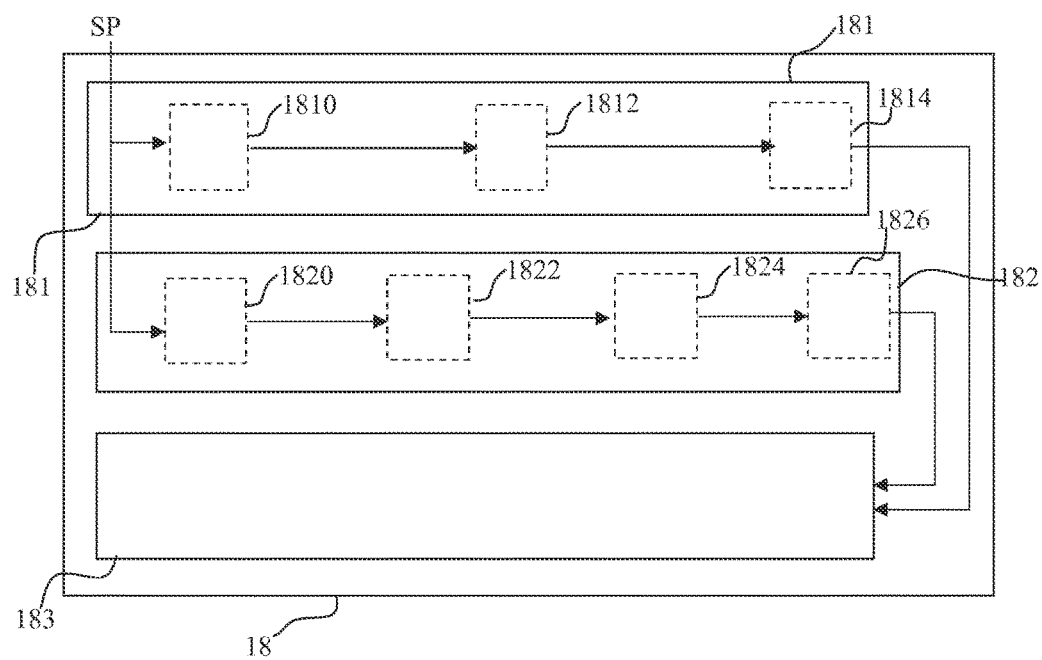
FIG. 2 is a diagram of an example of an analysis module according to the invention.

FIG. 2 is a diagram of an example of an analysis module 18.

The analysis module 18 comprises a saccade revealing sub-module 181. This saccade revealing module carries out:

a step 1810 of preliminary processing. The preliminary processing comprises:
performing Gaussian filtering of the position signal PS with a Gaussian filter of which the filter width may be parameterized by the user, then
taking a first derivative of the signal obtained by computing means.

a step 1812 of revealing "negative" saccades, i.e. horizontally towards the left, vertically downwards. Negative saccades are revealed as follows. So long as the derivative of the signal is negative, the values of the samples of that derivative are summed. If the velocity is less than the opposite of the velocity threshold value (which may be parameterized by the user, by default V<−30°/s) and if the sum computed previously exceeds the amplitude threshold value (which may be parameterized by the user, by default: A>5°), revealing or detecting bars are positioned on the first and last samples.

a step 1814 of revealing "positive" saccades, (horizontally towards the right, vertically upwards). Positive saccades are revealed as follows. So long as the derivative is positive, the values of the samples of the derivative signal are summed. If the velocity is greater than the velocity threshold value (which may be parameterized by the user, by default V>30°/s), and if the sum computed previously exceeds the amplitude threshold value (which may be parameterized by the user, by default: A>5°), revealing bars are positioned on the first and last samples.

The analysis module 18 further comprises an artefact revealing and eliminating module 182. This artefact revealing module 182 carries out:

a step 1820 of preliminary processing. The preliminary processing comprises:
performing Gaussian filtering of the position signal PS by a Gaussian filter having a filter width sigma=1, and
taking a first derivative of the signal obtained by computing means.

a step 1822 of revealing "negative" artefacts, horizontally towards the left, vertically downwards. The revealing of negative artefacts is carried out in the following manner. So long as the derivative is negative, the values of the samples of the derivative signal are summed. If the velocity is less than a threshold set by the user (−500°/s by default) and if the previously computed sum exceeds 5° and if the time between the first sample and the last is less than 200 ms, then revealing bars are positioned on the first and last samples.

a step 1824 of revealing "positive" artefacts, horizontally towards the right, vertically upwards. The revealing of positive artefacts is carried out in the following manner. So long as the derivative is positive, the values of the samples of the derivative signal are summed. If the velocity is greater than a threshold set by the user (500°/s by default) and if the previously computed sum exceeds 5° and if the time between the first sample and the last is less than 200 ms, then revealing bars are positioned on the first and last samples.

an artefact eliminating step 1826. The elimination of artefacts is carried out by retrieving the two samples corresponding to the start and to the end of the detected artefact. Let A and B be the points corresponding to those samples. The equation of the straight line (AB) is y=mx+p):

Computing the parameters "m" and "p" of the equation of the straight line (AB)

Copying of the samples preceding the point A.

Linear interpolation along the straight line (AB) between the points A and B while maintaining the same sampling frequency as that of the original signal.

Copying the samples following the point B up to the end of the signal.

Lastly, the analysis module comprises a sub-module 183 performing the computation of the oculomotor parameters on the basis of the data supplied by the saccade revealing sub-module 181 and the artefact revealing and eliminating sub-module 182, for different types of tests.

Of course, the revealing of the artefacts and the saccades may be performed by a single module. In that case, the artefacts are detected in the position signal PS and are then eliminated, before detecting the saccades.

The different types of tests are:
Gap,
Antisaccades,
Vertical saccades,
Smooth pursuit, The parameters measured for these different types of tests by the sub-module 183 for computing the parameters are the following:
average latency in ms (time for triggering the saccade after appearance of the visual stimulus)
average velocity in °/s of the saccades
maximum velocity in °/s of the saccades
percentage of errors (for the antisaccades)

Average Latency

Latency corresponds to the time in ms between the event (e.g. target positioned to the right) and the response by the eukaryote (bar for revealing saccade start).

The average latency is computed for the valid saccades:
Gap: a valid saccade corresponds to a saccade in which the eukaryote first looks towards the same side as the target (a distinction is drawn between average latency to the right and average latency to the left)

Antisaccades: a valid saccade corresponds to a saccade in which the eukaryote first looks towards the opposite side to the target (a distinction is drawn between average latency of the antisaccades target to the right and average latency of the antisaccades target to the left)

Vertical saccades: a valid saccade corresponds to a saccade in which the eukaryote first looks towards the same side as the target (a distinction is drawn between average latency upwards and average latency downwards)

Average Velocity

The average velocity is measured between the bar for revealing saccade start and the bar for revealing saccade end. The average velocity is computed for the valid latencies. A distinction is also made between average velocity to the left and to the right (gap and antisaccades) and upwards and downwards (vertical saccades).

Percentage of Errors.

For the antisaccades, if the eukaryote looks preferentially in the direction of the target, an error is counted.

A distinction is made between the percentage of errors of antisaccades target to the right and target to the left.

Figure 3:
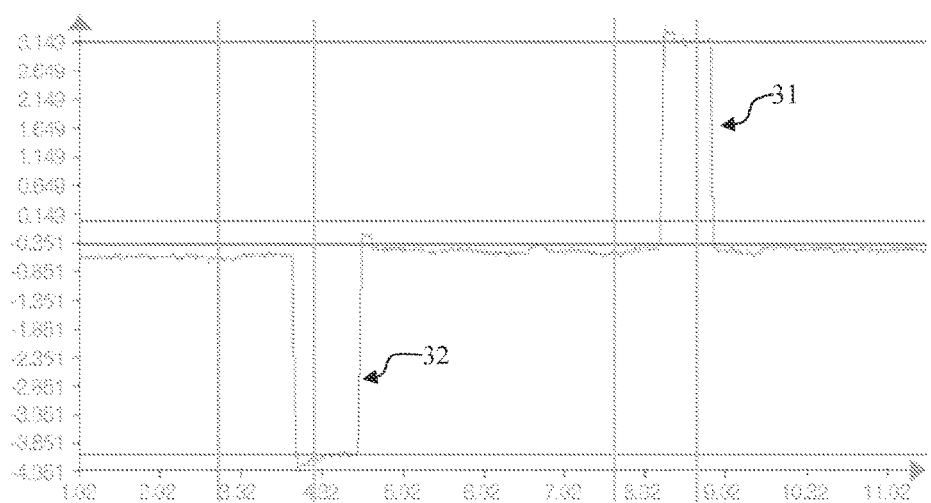
FIG. 3 is an example of a capture signal obtained with the system according to the invention.

FIG. 3 is an example of signal position obtained using the method and system according to the invention. In this Figure, two saccades 31 and 32 can be seen.

Lastly, on the basis of the data supplied by the analysis module 18 the diagnosis assistance module 22 determines a probability for each pathology and supplies a list of pathologies classified according to their probability on the basis of the results of the tests.

All the pathologies which may be detected with the invention, and for which the effectiveness and the follow-up of care may be evaluated, are neurological, psychiatric and neurodevelopmental pathologies, for example Parkinson's syndromes, Alzheimer's disease, Creutzfeld-Jacob's disease, dementia with Lewy bodies, intoxications, Tourette syndrome, schizophrenia, bipolar disorders, head injury, dyslexia, dyspraxia, etc.

The system according to the invention enables a visual examination to be taken and to record the ocular movements. The eukaryote looks at the stimulation images with instructions while the capture means record its oculomotor movements. The movements are instantaneously transformed into position of the visual cell on the screen and are recorded by the controlling computer. The supervised automatic revealing of the saccades and of certain parameters of oculomotricity, such as latency, the velocity of ocular movements, precision and errors, are then analyzed by artificial intelligence software which then proposes a probability index for classifying the patient's pathology.

The present system constitutes a companion test for remediation.

Naturally, the invention is not limited to the examples which have just been described and numerous modifications may be made to these examples without departing from the scope of the invention.

The invention claimed is:

1. A method for revealing oculomotor abnormalities in a human subject, said method comprising:
generating at least one visual stimulation image and displaying said at least one visual stimulation image on a display so that the image can be viewed by the subject;
the subject receiving a test instruction to perform an ocular test based on said at least one visual stimulation image, while viewing said at least one visual stimulation image on the display;
capturing eye movements of the subject with a capturing device while the subject is performing the ocular test according to the received test instruction and is viewing the at least one visual stimulation image, said capturing device supplying a capture signal of ocular movements;

transforming the capture signal supplied by the capturing device into a position signal indicating projection of the eye direction on the display while the subject is performing the ocular test according to the received test instruction and is viewing said least one visual stimulation image on the display;

with a computer, automatically computing a value of at least one predetermined parameter by analysis of said capture signal of ocular movements, wherein the analysis comprises revealing at least one saccade in the capture signal, and using the position signal to compute the value of the at least one predetermined parameter, wherein the analysis comprises revealing at least one artifact in the capture signal and eliminating said at least one artifact revealed in the capture signal of ocular movements, wherein the eliminating said detected artifact in said analysis includes:

determining a start sample and an end sample of an artifact in the capture signal of ocular movements, determining parameters of a straight line joining the start and end samples, copying samples of the capture signal preceding the start sample and samples of the capture signal following the end sample, and linear interpolating samples along the straight line between the start sample and the end sample while maintaining a same sampling frequency as a sampling frequency of the capture signal, so to eliminate the artifact from the capture signal; and determining an oculomotor abnormality in said subject based on said computed value and at least one predetermined value for the at least one predetermined parameter.

2. The method of claim 1, wherein the test is selected from a gap test, an antisaccade test and a vertical saccade test, the visual stimulation image comprises a target, and the computing a value comprises computing an average latency by analysis of said capture signal of ocular movements, the latency corresponding to a time elapsed between a trigger of a saccade after appearance of a corresponding visual stimulus, a valid saccade for the gap test corresponding to a saccade in which the subject first looks towards a same side, left or right, as the target, a valid saccade for the antisaccade test corresponding to a saccade in which the subject first looks towards an opposite side, left or right, as the target, a valid saccade for the vertical saccade test corresponding to a saccade in which the subject first looks towards a same side, up or down, as the target, the average latency value for the gap test, the antisaccade test and the vertical saccade test being computed for the corresponding valid saccades.

3. The method of claim 2, wherein the computing comprises computing for the gap test average latency to the right and average latency to the left.

4. The method of claim 2, wherein the computing comprises computing for the antisaccade test average latency target to the right and average latency target to the left.

5. The method of claim 2, wherein the computing comprises computing for the vertical saccade test average latency upwards and average latency downwards.

6. The method of claim 2, wherein the computing comprising computing an average velocity for the corresponding valid saccades.

7. The method of claim 6, wherein the computing comprises computing for the gap test or the antisaccade test average velocity to the right and average velocity to the left.

8. The method of claim 2, wherein the computing comprises computing for the antisaccade test a percentage of errors, an error being when the subject looks in the direction of the target.

9. The method of claim 8, wherein the computing comprises computing for the antisaccade test the percentage of error of antisaccades target to the right and target to the left.

10. The method of claim 2, wherein each one of the gap test, antisaccade test and vertical saccade test is performed.

11. The method of claim 1, comprising determining a probability of a pathology.

12. The method of claim 11, comprising determining a list of pathologies classified according to their probability based on the result of the tests.

13. The method of claim 11, the pathology being selected from the group consisting of Parkinson's syndromes, Alzheimer's disease, Creutztfeld-Jacob's disease, dementia with Lewy bodies, intoxications, Tourette syndrome, schizophrenia, bipolar disorders, head injury, dyslexia, and dyspraxia.

14. The method of claim 1, comprising determining a precision of saccades as a distance to the target.

15. The method of claim 1, comprising determining a presence of isolated saccades which interrupt fixation very briefly and fast return to the fixation.

16. The method of claim 1, comprising determining a presence of nystagmus.

17. The method of claim 1, comprising performing a pursuit test and determining at least one of a pursuit phase shift, a quality of pursuit and a pursuit gain representing an amplitude of ocular movement during a slip of the visual stimulus in the image.

18. The method of claim 1, comprising displaying results relative to said tests carried out over time by the subject to enable a comparison between the results.

19. The method of claim 1, the display and the capturing device being in the form of binoculars, glasses or a glass frame worn by the subject during the test.

* * * * *